United States Patent [19]

Tice, Jr. et al.

[11] Patent Number: 5,064,519

[45] Date of Patent: Nov. 12, 1991

[54] NEUTRAL AND POSITIVELY CHARGED DYES FOR ELECTROPHORESIS SAMPLE LOADING SOLUTIONS

[75] Inventors: George Tice, Jr., Wenonah, N.J.; Douglas A. Amorese, Hockessin, Del.

[73] Assignee: E. I. du Pont de Nemours and Company, Wilmington, Del.

[21] Appl. No.: 546,186

[22] Filed: Jun. 29, 1990

[51] Int. Cl.$^5$ .............................. C25B 1/00; C25B 7/00
[52] U.S. Cl. ................................ 204/182.8; 204/180.1
[58] Field of Search ........................... 204/182.8, 180.1

[56] References Cited

U.S. PATENT DOCUMENTS

| | | | |
|---|---|---|---|
| 3,948,743 | 4/1976 | Monthony et al. | 204/182.8 |
| 4,124,470 | 11/1978 | Dahms | 204/180.1 |
| 4,306,956 | 12/1981 | de Castro et al. | 204/182.8 |
| 4,582,868 | 4/1986 | Ogawa et al. | 204/182.8 |

OTHER PUBLICATIONS

John L. Couch et al., Anal. Biochem., vol. 41, p. 51 (1971).
J. Sanbrook et al., Molecular Cloning: A Laboratory Manual, Cold Spring Harbor Press, pp. 6–12 (1989).
J. M. Prober et al., Science, vol. 238, pp. 336–341 (1978).
M. Dubois et al., Analytical Chemistry, vol. 28, pp. 350–356 (1956).
C. Tsai et al., Analytical Biochemistry, vol. 119, pp. 115–119 (1982).
U. K. Laemmli, Nature, vol. 227, pp. 680–685 (1970).
F. Sanger et al., Proc. Nat. Acad. Sci., U.S.A., vol. 74, pp. 5463–5467 (1977).
P. S. Thomas, Proc. Nat. Acad. Sci., vol. 77, pp. 5201–5212 (1980).

*Primary Examiner*—John Niebling
*Assistant Examiner*—Caroline Koestner

[57] ABSTRACT

A method of electrophoretically separating bioorganic molecules is disclosed. The method uses a slab electrophoresis gel and positively or neutrally charged dyes to prevent the dyes from interfering with the gel readout.

7 Claims, No Drawings

NEUTRAL AND POSITIVELY CHARGED DYES FOR ELECTROPHORESIS SAMPLE LOADING SOLUTIONS

FIELD OF THE INVENTION

This invention relates to a method of using neutral or positively charged dyes to facilitate the loading of a sample onto a gel matrix for separation by electrophoresis.

BACKGROUND OF THE INVENTION

Electrophoresis is a separation process well known in the art (C. F. Simpson, *Electrophoretic Techniques*, Academic Press, New York (1983)) and is achieved by passing an electric current through a porous matrix to which the compounds to be separated have been applied. The compounds migrate through the matrix at a rate that is dependent upon the size and/or charge to mass ratio of the compound and the strength of the electric field that is applied to the matrix. This technique can be used to separate small compounds including carbohydrates and amino acids, as well as large macromolecules such as polysaccharides, proteins, DNA, and RNA (M. Dubois et al., *Analytical Chemistry* 28, 350-356, (1956), C. Tsai et al., *Analytical Biochemistry* 227, 115-119 (1982), U. K. Laemmli, Nature, 227, 680-685 (1970), F. Sanger et al., *Proc. Nat. Acad. Sci. U.S.A.* 74. 5463-5467 (1977), P. S. Thomas, *Proc. Nat. Acad. Sci.* 77, 5201-5212 (1980)). Various matrices can be used for the separation of compounds by electrophoresis including paper, starch, agarose, and polyacrylamide.

Electrophoretic separation generally includes the following steps: the separation gel or matrix is equilibrated with a suitable electrophoresis buffer that will be used during the electrophoresis process, each end of the equilibrated matrix is placed in contact with a reservoir also containing a buffer, a positive electrical lead is placed in one of the reservoirs while the second reservoir has a negative lead attached, the samples are applied to the matrix, and an electric field is generated (C. F. Simpson, *Electrophoretic Techniques*, Academic Press, New York (1983)). Once the electrophoretic separation is completed, the separated compounds can be visualized by a variety of different methods (M. Dubois et al., *Analytical Chemistry* 18, 350-356 (1956), C. Tsai et al., *Analytical Biochemistry* 119, 115-119 (1982), S. M. Hassur et al., *Anal. Biochem.* 41, 51 (1971)).

In many electrophoresis separation systems, the samples are applied to a small well which is formed in the matrix to provide a guide for loading the sample. This sample well is typically submerged with the electrophoresis buffer. A suitable loading solution therefore needs to have a density that is greater than that of the electrophoresis buffer. Other components of a suitable loading solution include reagents that stabilize or denature the sample. To meet these needs, substances such as formamide, glycerol, ficoll, sucrose, SDS, or urea are typically added in the loading solution. In addition, it is desirable to include as a component of a loading solution, a dye that facilitates visualization of the sample during the loading process. The addition of a colored dye to the loading solution allows easy visualization of the solution as it is applied to the sample well. Among the dyes that have been used in loading solutions, include bromophenol blue and xylene cyananol (J. Sanbrook et al., *Molecular Cloning: A Laboratory Manual*, Cold Spring Harbor Press, 6-12 (1989)). These dyes migrate in the electric field during electrophoresis and can be used to estimate the distance the compounds have migrated through the matrix.

Recently, systems have been developed that rely on detection of the compounds as they migrate through the matrix. These systems have fixed detection zone(s) that typically employ the use of photomultiplier tubes to detect light (J. M. Prober et al., *Science*, Vol. 238, 336-341 (1978)). Dyes known in the art (J. Sanbrook et al., *Molecular Cloning: A Laboratory Manual*, Cold Spring Harbor Press, 6-12 (1989)) can interfere with the detection of compounds that migrate through the detection zone at or near the same point in time as the dye. Thus, there is need for dyes which facilitate the loading of samples onto a matrix but which do not interfere with the detection of compounds.

SUMMARY OF THE INVENTION

The use of dyes to facilitate loading of a sample onto an electrophoresis gel for electrophoretic separation without interfering with detection of the separated bioorganic molecules is greatly facilitated by the use of the method of this invention. The invention uses dyes which are positively charged or neutral (in solution) which do not enter the gel because of their charge, the bioorganic molecules being negatively-charged. During electrophoresis the dyes and the bioorganic molecules move differently. If positively charged dyes are used, the bioorganic molecule and dye move in different directions. If neutrally charged dyes are used, the dyes simply do not enter the gel and only the bioorganic molecules are driven through the gel by the influence of the electric field. There is hence little or no interference between the electrophoretically separated bioorganic molecules and the dyes.

In accordance with this invention a method of electrophoretically separating bioorganic molecules is disclosed using a slab of a porous electrophoresis gel in buffer, the gel having length and width dimensions and defining plural wells adapted to receive samples for separation, comprising the steps of: adding a sample of bioorganic molecules to be separated to a solution containing a dye, wherein the net charge of dye in solution is neutral or positive, to provide a loading solution, introducing an aliquot of the loading solution to one of the wells with the visual aid of the dye, and applying a voltage across one of the gel dimensions, whereby the dye and bioorganic molecules are driven by the voltage differently to reduce interference between the dye and the bioorganic molecules.

The positively-charged dyes may be selected from a large number of dyes including Brilliant Green, Methyl Blue, Methyl Green, Bismark Brown Y, Bismark Brown R, Malchite Green, Neutral Red, Tolonium Chloride, and Crystal Violet. Likewise, the neutral dyes may be selected from a large number of dyes, including Acramine Yellow, Sudan III, Alizarine Blue, Alizarine Orange, Gallacetophenone, Hematoxylin, Scarlet Red, Alizarin, Gallein, and Blue Dextran. Finally, any of the known buffers may be used to provide a net charge of the dye in solution that is either positive or neutral so that the dyes will not interfere with the separated bioorganic molecules.

DETAILED DESCRIPTION OF THE PREFERRED METHOD

A preferred dye according to this invention is crystal violet. The method of this invention may be used with any electrophoretic separation system. According to the method of this invention bioorganic molecules, i.e., molecules which have a negative charge and include amino acids, DNA, proteins, etc., are separated by placing them on a column or slab of a porous electrophoresis gel in an appropriate buffer. Although any gel of this type may be used, this invention has greater utility with slab gels which normally have parallel channels, each defining a separate well, into which a sample of a bioorganic molecule is introduced. The wells are usually disposed along one side of either the length or width dimension of the slab gel. Regardless of the type of gel used, according to this invention, the sample or organic molecules to be separated are added to a solution containing a neutral or positively charged dye and buffer to provide a solution for loading the sample onto the gel for separation. An aliquot of the loading solution is placed on the slab gel usually at a location of one of the wells. The color of the dye aids in this placement. Finally a voltage is applied across one of the gel dimensions (generally perpendicular to the line of the wells) thus permitting the dye and bioorganic molecules to be driven differently. If a positively-charged dye is used, such that the net charge of the dye in solution is positive, the molecules and the dye are driven in opposite directions, the molecules being driven towards the positive terminal of the applied voltage. If a neutral dye is used, such that the net charged in solution is positive, the dye does not migrate on the slab and the bioorganic molecules migrate toward the positive terminal. In each case, the molecules and dye acting differently are kept totally separate and there is little or no interference with detection of the bioorganic molecules that separated from the dye.

There are many positive-charged dyes that may be used with this invention. These include Brilliant Green, Methyl Blue, Methyl Green, Bismark Brown Y, Bismark Brown R, Malchite Green, Neutral Red, Tolonium Chloride, and Crystal Violet. In similar manner any neutral dyes may also be used. These include Acramine Yellow, Sudan III, Alizarine Blue, Alizarine Orange, Gallacetophenone, Hematoxylin, Scarlet Red, Alizarin, Gallein, and Blue Dextran. It is also within the scope of this invention to use a negatively charged dye so long as the net charge of the dye in buffer solution is neutral. Both dyes may be obtained from Sigma Chemical Co.

The preferred dye is crystal violet (a positively charged dye) for use with this invention at a concentration of 0.1 mg/mL. The preferred neutral dye is blue dextran at a concentration of 3 mg/mL. Formamide is the preferred buffer. Any concentration providing for visualization of the sample loading solution can be used.

The preferred electrophoresis system for practicing this invention is the Genesis ® 2000 DNA Sequence, available from E. I. du Pont de Nemours and Company. However, the method of using the dyes of this invention can be used with any electrophoresis separation system.

In its preferred embodiment, a 95% formamide solution containing crystal violet at a final concentration of 0.1 mg/ml is applied to a well of a 6% polyacrylamide gel that had been previously run for 30 minutes at a constant power of 18 watts in a Genesis ® 2000 DNA Analysis instrument. Tris-Borate-EDTA (TBE) buffer is preferentially used as the electrophoresis buffer. The sample is dissolved in the loading solution containing the dye, then loaded into a well in the electrophoresis gel matrix, and the gel subjected to electrophoresis.

EXAMPLE 1

Solutions of crystal violet (Sigma Chemical Company), a positive dye, in 0.2M EDTA, pH 8.0, of 4 mg/ml, 2 mg/ml, 1 mg/ml and 0.5 mg/ml were prepared. A 50 µl aliquot of each solution was diluted with 950 µl of a 95% deionized formamide solution. Each of the diluted crystal violet solutions was qualitatively analyzed for color intensity by introducing 3 µl of the formamide-containing solution to a well in a 6% polyacrylamide gel matrix (prepared by making a solution containing 15 gm urea, 11.5 mL water and 4.5 mL 40% acrylamide, adding 0.5 gm AG 501-X8 de-ionizing resin (Bio-Rad Company), filtering the solution, adding 3 mL 10 X TBE, and de-gassing by vacuum). Tris-Borate-EDTA (TBE) buffer (pH=8.3) (Digene Company) was used as the electrophoresis buffer. The lowest concentration of crystal violet that was sufficient in facilitating the visualization of sample loading was the 2 mg/ml crystal violet solution. This concentration of crystal violet, diluted with deionized formamide, as described, to provide final concentration of crystal violet of 0.1 mg/ml was used for the further characterization of the dye containing loading solution.

EXAMPLE 2

A 3 µl aliquot of the loading solution of Example 1 (conc. 0.1 mg/ml) was applied to a well of a 6% polyacrylamide gel that had been previously run for 30 minutes at a constant power of 18 watts in a Genesis ® 2000 DNA Sequencer. TBE buffer was used as the electrophoresis buffer. The sample was loaded, the door of the gel chamber of the Genesis ® 2000 DNA Sequencer was closed and the gel was then electrophoresed at 18 watts. The electrophoresis was paused at 2 minutes, the gel chamber door was opened, and the wells were visually examined for the presence of dye. The examination revealed that the dye had started to migrate out of the well towards the upper buffer reservoir and away from the gel matrix.

EXAMPLE 3

To determine the effect of the crystal violet on sample resolution in the gel matrix, fluorescent DNA fragments were dissolved in the loading solution of Example 1 (conc. 0.1 mg/ml) and applied to a standard DNA sequencing gel as described in the Detailed Description of the Preferred Embodiment. The fluorescent DNA samples were prepared by mixing 3 µg DNA, 15 ng Sequencing primer, and 5X Sequenase ® buffer (available as components in the Genesis ® 2000 DNA Sequencing kit from Du Pont), heating to 95° C. for 2 minutes, annealing at 37° C. for 10 minutes, adding 3 µl deoxy nucleotides (Genesis ® 2000 DNA Sequencing kit from Du Pont) (75 µm), 1 µl fluorescent dideoxy nucleotides (Dideoxy Mix) (Genesis ® 2000 DNA Sequencing kit from Du Pont), 2.5 µl dithiothreitol (0.1M) and 1 µl (3 units) of Sequenase ® (Genesis ® 2000 DNA Sequencing kit from Du Pont), and incubating at 37° C. for 5 minutes. Following the 5 minute elongation step, excess fluorescent dideoxy nucleotides were removed by ethanol precipitation of the DNA by the following procedure: 30 µl of 5M ammonium acetate and 150 μl of absolute ethanol at −20° C. were added to the tube, the tube was vortexed and centrifuged in a table top microcentrifuge for 15 minutes (12,000×g) at room temperature, the supernatant was aspirated by vacuum, the resulting DNA pellet was washed with 500 μl of 75% ethanol (−20° C.) and centrifuged for 10 minutes (12,000×g) at room temperature, the supernatant was aspirated by vacuum, and the pellet was dried in a Savant rotary evaporation centrifuge for 3 minutes.

The dried fluorescently labelled DNA pellets were solubilized with 3 μl of loading solution (95% deionized formamide, 10 mM EDTA pH=8.0) prepared as in Example 1). The loading solution was prepared with and without crystal violet (0.1 mg/ml final concentration). The samples were denatured at 95° C. for 2 minutes and applied to a 6% polyacrylamide gel that had been previously run for 30 minutes at 18 watts in a Genesis ® 2000 DNA Sequencer. The samples were then electrophoresed for 8 hours at a constant power of 18 watts. Data was collected, stored and processed on a MAC II computer which is part of the Genesis ® 2000 DNA Sequencer. Table 1 indicates that neither the length of the run, number of DNA fragments detected, or the accuracy of the run were effected by the addition of crystal violet to the loading solution.

TABLE 1*

| LOADING SOLUTION | ERRORS | | |
|---|---|---|---|
| | 300 bases | 350 bases | 400 bases |
| Control | 1 | 2 | 7 |
| Crystal Violet | 1 | 2 | 7 |

*All results shown for electrophoresis runs using the Genesis ™ 2000 DNA Sequencer.

EXAMPLE 4

The same procedure as described in Example 3 was applied for the dye blue dextran (Pharmacia Company), a neutral dye. A concentration of blue dextran of 60 mg/ml was used. The results are shown in Table 2. Table 2 indicates that neither the length of the run, number of DNA fragments detected, or the accuracy of the run were effected by the addition of blue dextran to the loading solution.

TABLE 2*

| LOADING SOLUTION | ERRORS | | |
|---|---|---|---|
| | 300 bases | 350 bases | 400 bases |
| Control | 1 | 2 | 7 |
| Blue Dextran | 1 | 5 | 7 |

*All results shown for electrophoresis runs using the Genesis ™ 2000 DNA Sequencer.

What is claimed is:

1. A method of electrophoretically separating biomolecules using a slab of a porous electrophoresis gel in buffer, the gel having length and width dimensions and defining plural wells adapted to receive samples for separation, comprising the steps of:

adding a sample of bioorganic molecules to be separated to a solution containing a charged dye wherein the net charge of the dye in solution is neutral or positive, thereby to provide a loading solution, introducing an aliquot of the loading solution to one of the wells with the aid of the dye, and applying a voltage across one of the gel dimensions to cause the bioorganic molecules to migrate through that gel dimension in a first directional sense and the dye molecules either not to migrate in the gel or to migrate in a second directional sense in the opposite direction to the first directional sense, whereby the dye and the bioorganic molecules are driven differently to reduce interference between the dye and the bioorganic molecules.

2. A method according to claim 1 wherein the dye is positively charged and are selected from the group consisting essentially of Brilliant Green, Methyl Blue, Methyl Green, Bismark Brown Y, Bismark Brown R, Malchite Green, Neutral Red, Tolonium Chloride, and Crystal Violet.

3. A method according to claim 1 wherein the dye is neutral and selected from the group consisting essentially of Acramine Yellow, Sudan III, Alizarine Blue, Alizarine Orange, Gallacetophenone, Hematoxylin, Scarlet Red, Alizarin, Gallein, and Blue Dextran.

4. A method according to claim 1 wherein the dye is crystal violet.

5. A method according to claim 1 wherein the dye is blue dextran.

6. A method according to claim 1 wherein the loading solution includes formamide.

7. A method according to claim 1 wherein the dye in solution is neutral.

* * * * *